United States Patent [19]
Suddath et al.

[11] Patent Number: 5,239,877
[45] Date of Patent: Aug. 31, 1993

[54] GAS EMISSION SAMPLE CONTAINER WITH INTERNAL MIXING FITTING

[75] Inventors: James N. Suddath, West Bloomfield; William T. Vecere, Royal Oak, both of Mich.

[73] Assignee: Engineered Devices, Inc., Royal Oak, Mich.

[21] Appl. No.: 905,900

[22] Filed: Jun. 26, 1992

[51] Int. Cl.$^5$ ............................................. G01N 1/00
[52] U.S. Cl. ............................. 73/864.62; 137/561 A; 383/906
[58] Field of Search ............ 73/864.51, 864.62, 864.63, 73/864.91; 383/3, 41, 109, 904, 906; 137/561 A, 590, 592

[56] References Cited

U.S. PATENT DOCUMENTS

| | | | |
|---|---|---|---|
| 2,602,465 | 7/1952 | Goehring | 137/592 |
| 3,603,155 | 9/1971 | Morris et al. | 73/421.5 R |
| 3,977,708 | 8/1976 | Jopp | 285/342 |
| 4,546,659 | 10/1985 | Gill et al. | 73/864.62 |
| 4,817,423 | 4/1989 | Christiansen | 73/153 |
| 4,998,990 | 3/1991 | Richter et al. | 383/906 |
| 5,074,155 | 12/1991 | Vecere | 73/864.62 |

Primary Examiner—Robert Raevis
Attorney, Agent, or Firm—Basile and Hanlon

[57] ABSTRACT

A gas emission sample container includes first and second flexible sheets sealed at their peripheral edges to form a closed interior cavity. A plurality of spaced, discrete projections are formed in at least one of the sheets and extend inward to the interior cavity toward the opposed sheet. Gas flow paths are formed between adjacent projections on the one sheet within the interior cavity for complete inflation and evacuation of the container. A fitting is mounted in the interior cavity in the container and includes a body with top and bottom surfaces curving smoothly to a peripheral edge. A first bore extends centrally through the top surface into the body of the fitting. A plurality of second bores are formed in the body and extend tangentially from the first bore to the peripheral edge of the body to dispose of the first bore in fluid communication with the interior of the container.

18 Claims, 3 Drawing Sheets

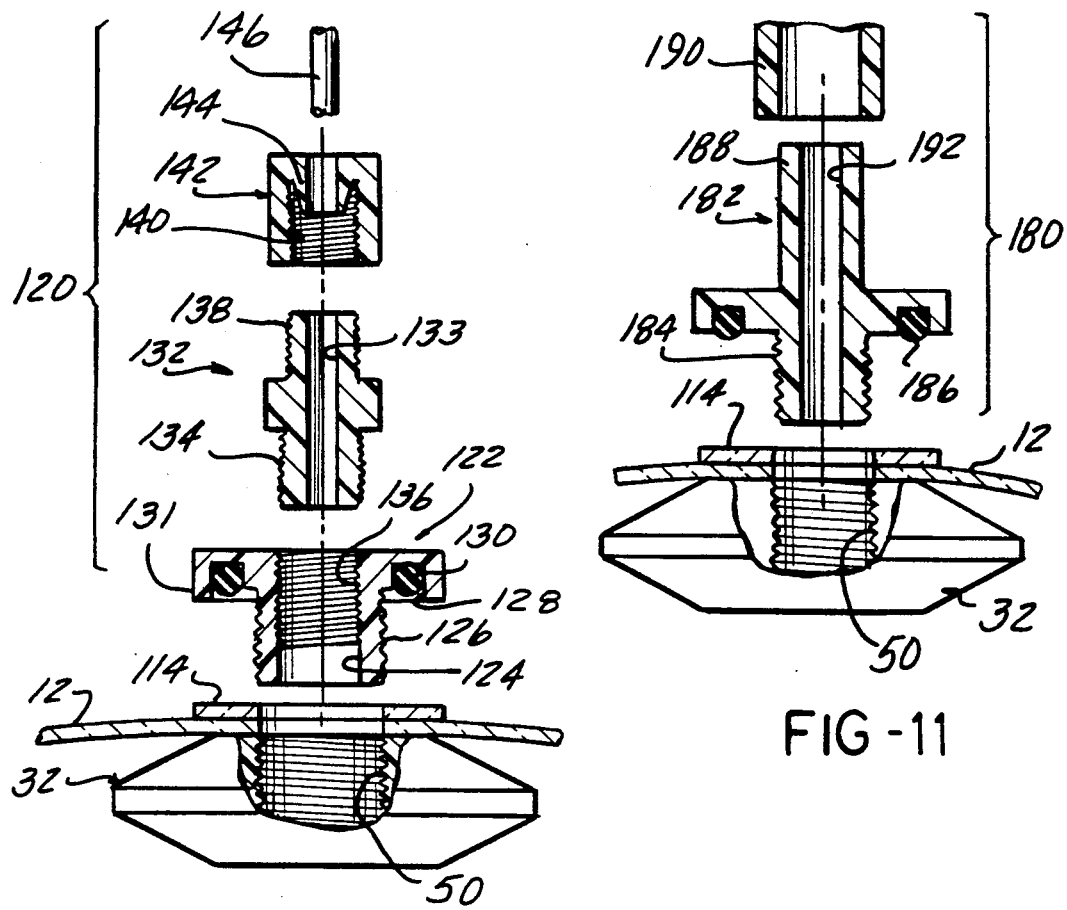
FIG-9
FIG-11
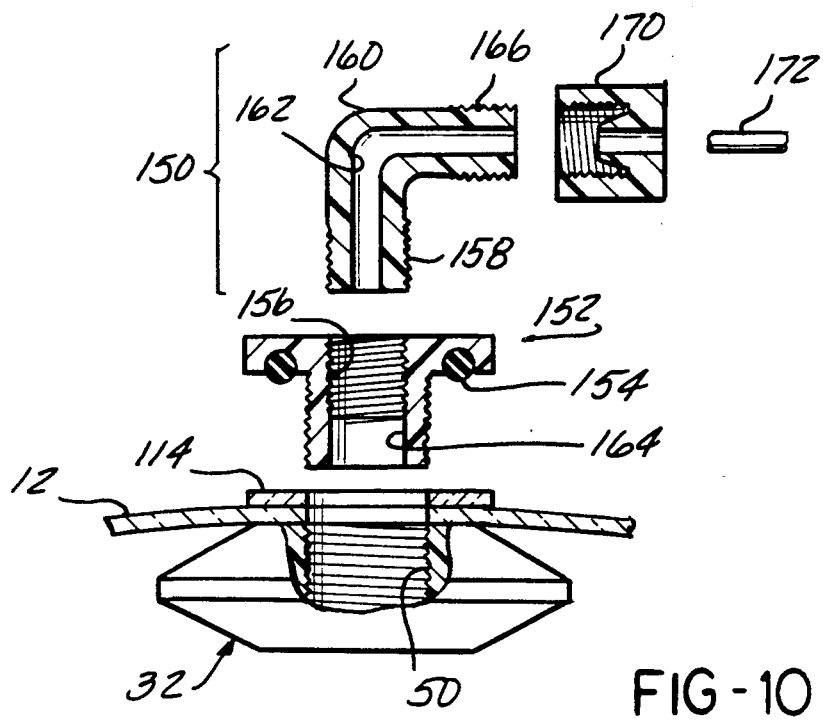
FIG-10

GAS EMISSION SAMPLE CONTAINER WITH INTERNAL MIXING FITTING

BACKGROUND OF THE INVENTION

1. Field of the Invention

The present invention relates to gas emission sample containers for collecting gas emissions from motor vehicles.

2. State of the Art

Expandable, sealed containers or bags are employed for collecting and temporarily storing gas emissions from motor vehicles before the collected emissions are analyzed by suitable test equipment. Such containers are expandable to a predetermined volume to collect a known quantity of gaseous emissions.

Typically, a plurality of such containers, such as six containers, are connected through suitable conduits, valves, etc., to a test apparatus to collect separate quantities of gas emissions from a vehicle and from ambient atmosphere. Samples of emissions from a motor vehicle under test are collected in the sealed containers as the motor vehicle is operated according to a prescribed test schedule corresponding to various engine operating conditions.

The expandable containers include a fitting sealingly mounted in each container which is connected to the test apparatus to receive gas emissions from the vehicle under test. The fitting directs the gas emissions into the container for storage, as well as enabling the stored gas contents to be evacuated from the container for subsequent analysis. The fitting and the sealed container are made of a chemically inert material, such as a fluorinated carbon plastic, i.e., plastics sold under the registered trademarks TEFLON, KYNAR, and/or TEDLAR.

In order to prevent wrinkling of the container when it is evacuated of gas and to insure complete inflation of the container to a constant volume without internal dead spots, small diameter, hollow conduits or tubes are disposed within the sealed container and connected in fluid flow communication with the fitting. The conduits have apertures formed along their lengths to draw gas from different parts of the container to prevent stratification of the gas within the container and to insure thorough mixing of the gas. Such conduits have been provided in a variety of shapes, such as a plurality of circumferentially spaced, straight segments, curved segments, etc.

An example of a fitting and gas conduit arrangement suitable for use in a gas emission sample apparatus is disclosed in U.S. Pat. No. 5,074,155. The fitting disclosed in this application has a small, smoothly tapered shape which minimizes dead spots in the container in the area of the fitting. Further, gas flow ports are formed in the fitting and receive gas conduits such that the gas conduits are arranged in a predetermined shape within the container to insure complete filling of the container to a constant volume and the complete evacuation of the stored gas from the container.

However, small gas emission containers for small sample volumes do not have sufficient interior space to enable the use of a gas flow conduit or conduits therein. Further, the economics of such small sample containers dictate away from the use of gas flow conduits and the associated, more complex fittings. However, such small gas emission containers must still be filled to a constant volume and, also, be completely evacuated of the gas contents for accurate test results. During storage and, particularly, during evacuation of the gas from the container, it is also important that the gas be distributed equally to all parts of the container and withdrawn from all parts of the container to overcome any stratification of the gaseous components that may occur.

Thus, it would be desirable to provide a container for a gas emission sample apparatus which overcomes the problems associated with previously devised containers insofar as enabling complete filling of the container to a predetermined volume and complete evacuation of the container without the necessity of mounting a gas flow conduit internally within the container. It would also be desirable to provide a container for a gas emission sample apparatus which can be simply constructed at a low manufacturing cost. It would also be desirable to provide a gas emission sample container with an internal mixing fitting which provides complete mixing of the gas stored in the container during storage and/or evacuation.

SUMMARY OF THE INVENTION

The present invention is a gas emission sample container with an internal mixing fitting.

The gas emission sample container includes a sealed, expandable body having an aperture formed in one wall. The sealed container is preferably formed of single-ply top and bottom, flexible, plastic sheets. The top and bottom sheets are sealingly connected at all of their peripheral edges to the sealed container.

At least one of the two sheets forming the container is formed with a plurality of spaced projections extending from one surface of the sheet. The projections extend toward the other sheet of the container when the two sheets are joined together at their peripheral edges to form the container. Spaces between adjacent projections on the one sheet form gas flow paths over the entire surface of the one sheet which insures the complete filling and the complete evacuation of gas to and from the container.

The projections may be formed of irregular shapes and disposed at irregular spacings over the one sheet. Alternately, the projections may have an identical shape and be disposed at a constant spacing in a predetermined pattern over the entire surface of the one sheet. Further, both of the sheets formed in the container may have projections formed thereon, with the projections facing each other in the interior of the container.

In a preferred embodiment, a fitting is disposed internally within the sealed container. The fitting is in the form of a body having a circular plan shape with smooth top and bottom surfaces meeting at a common peripheral edge.

A first bore is formed in the body and extends through the top surface of the body into the interior of the body. A plurality of circumferentially spaced, second bores are also formed in the body. The second bores are disposed in fluid flow communication at one end with the first bore and extend tangentially from the first bore radially outward to the peripheral edge of the body. The outer end of each of the second bores forms a gas flow port which disposes the first bore and each of the second bores in fluid flow communication with the interior cavity within the sealed container.

In an exemplary embodiment, the first end of each of the second bores is disposed in fluid flow communication in a tangential manner with a bottom portion of the first bore. Each of the second bores preferably extends upward at an acute angle with respect to longitudinal axis of the first bore to the peripheral edge of the body. Preferably, the acute angle is substantially 75° with respect to the longitudinal axis of the first bore.

The unique gas emission sample container with internal mixing fitting of the present invention provides even distribution and mixing of the gas during the flow of the gas through the fitting into the interior of the sealed container as well as during evacuation of the stored gas through the fitting to a gas test apparatus. More importantly, during evacuation of the stored gases, the tangential arrangement of the gas flow ports and the second bores in the fitting insures that the stored gas is drawn evenly from all portions of the container and mixed within the first bore of the fitting by a swirling action imparted by the tangential arrangement of the second bores with respect to the first bore to overcome the adverse effects of any stratification of the gas within the container.

The gas emission sample container with internal mixing fitting of the present invention provides substantially zero dead volume within the gas emission container so as to enable accurate test results with a known volume of gas to be obtained.

The tangential arrangement of gas flow ports and second bores in the fitting of the present invention enables a gas emission sample container to be constructed without the need for internal conduits to distribute the gas evenly throughout the container as well as to draw the gas evenly from all portions of the container during evacuation of the gas. This is ideal for small volume gas emission sample containers which typically do not utilize gas flow conduits within the container due to volume constraints.

The construction of the gas emission sample container with at least one sheet having spaced projections formed therein prevents wrinkling and dead spots during evacuation of the gas so as to provide more accurate test results.

BRIEF DESCRIPTION OF THE DRAWING

The various features, advantages and other uses of the present invention will become more apparent by referring to the following detailed description and drawing in which:

FIG. 9 is a partially cross-sectioned exploded view of another embodiment of a coupling usable with the fitting of the present invention;

FIG. 10 is a partially cross-sectioned, exploded view of another embodiment of a coupling; and FIG. 11 is a partially cross-sectioned, exploded view of yet another coupling usable with the fitting of the present invention.

DESCRIPTION OF THE PREFERRED EMBODIMENTS

Figure 1:
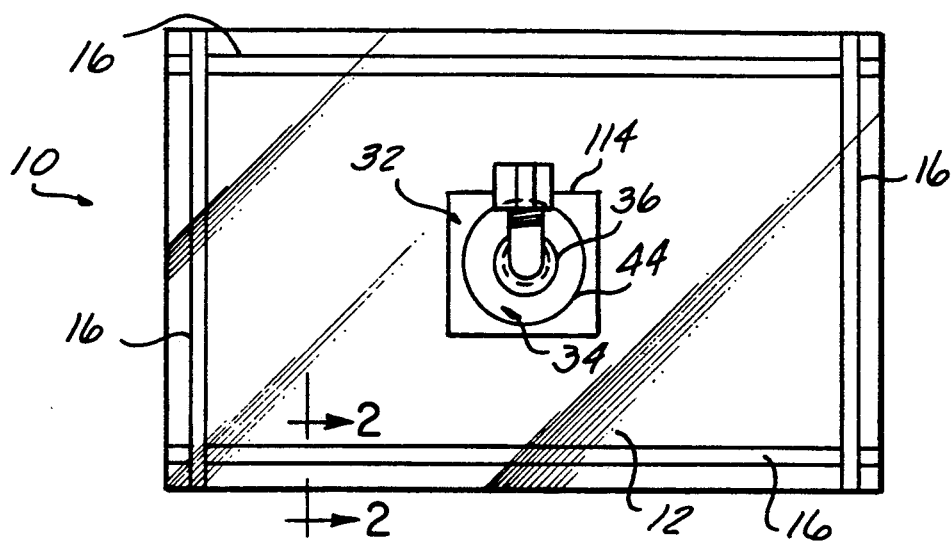
FIG. 1 is a plan view of a sealed gas emission sample apparatus utilizing a container constructed in accordance with the present invention.

Referring now to the drawing, and to FIG. 1 in particular, there is illustrated a gas emission sample container 10 which is connectible to suitable test equipment, not shown, to collect and temporarily store gas emissions from a motor vehicle, or other source, prior to the evacuation of such stored gas emissions for subsequent analysis.

Figure 2:
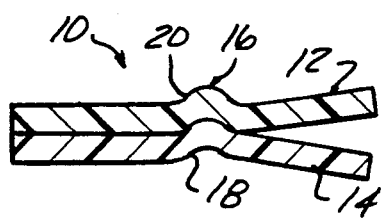
FIG. 2 is a cross sectional view generally taken along line 2—2 in FIG. 1.

As shown in FIGS. 1 and 2, the gas emission sample container 10 comprises a sealed enclosure of any shape, such as rectangular, square, circular, etc. It will be understood that a rectangular shape for the container 10 is illustrated by way of example only. Further, the container 10 may be provided in different sizes depending upon the requirements of a particular test application.

The sealed container or bag 10 is formed of two flexible sheets of chemically inert material. Preferably, fluorinated plastics chosen from the fluorocarbon family, such as those sold under the trademarks TEFLON, TEDLAR and HALON, may be employed. As shown in FIG. 2, the sealed container 10 is formed of a top or upper sheet 12 and a lower or bottom sheet 14 of a single thickness or ply. Typically, the single ply sheets 12 and 14 are 2 or 4 mils. in thickness. The upper and bottom sheets 12 and 14, respectively, are sealingly connected at their peripheral edges by any suitable means, such as by the depicted heat seam 16. Such a sealing method forms a recess 18 on one side of the joined sheets 12 and 14 and a small projection or bump 20 on the opposite surface. For additional sealing capability, two spaced heat seams 16 may be employed about the peripheral edges of the upper and bottom sheets 12 and 14. The seam or seams 16 seal the peripheral edges of the upper and bottom sheets 12 and 14 and form a hollow, expandable, internal cavity 22, FIG. 4, within the interior of the sealed container 10.

Figure 3:
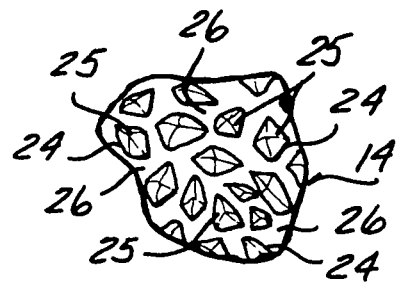
FIG. 3 is a partial, enlarged pictorial representation of one embodiment of the projections formed on one sheet of the container of the present invention.

According to the present invention, at least one of the sheets, such as the second sheet 14 of the container 10, includes a plurality of spaced, discrete projections 24, as shown in FIG. 3. The projections 24 extend outward from one surface of the sheet 14 toward the opposed sheet 12 in the interior cavity 22 of the sealed container 10. The projections 24 may have irregular shapes and may be disposed at irregular spacings as shown in FIG. 3. However, the projections 24 are formed on substantially the entire surface of the sheet 14.

Figure 4:
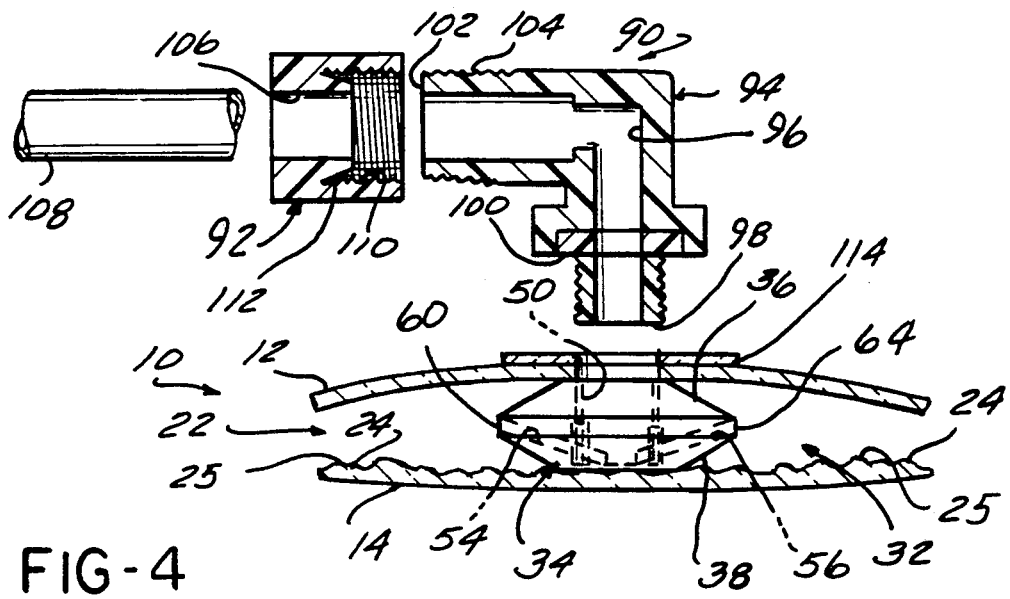
FIG. 4 is a partial, exploded, front elevational view showing the mounting of the fitting within the sealed container and the attachment of the coupling to the fitting.

The projections 24 are formed in the sheet 14 by any suitable means, such as the use of rolls or a press which permanently deforms the sheet 14 into the desired projection shape and location. As shown in FIGS. 3 and 4, the projections 24 generally taper from the surface of the sheet 14 to an apex 25. It will be understood that projections 24 having any other shape may also be employed to practice the present invention.

As shown in FIG. 3, a plurality of gas flow paths 26 are formed between the spaced, adjacent projections 24. The gas flow paths 26 extend over the entire surface of the sheet 14 and remain even when the container 10 is evacuated and the opposed sheet 12 is drawn into close registry or contact with the sheet 14. The gas flow paths 26 thus insure a complete filling of the container 10 when gas is introduced into the interior cavity 22 of the container 10 through a fitting 32 as well as a complete evacuation of the entire volume of gas from the container 10 through the fitting 32.

Figure 5:
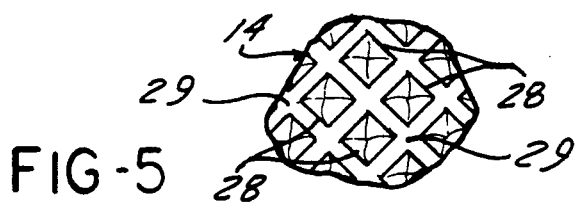
FIG. 5 is a partial, enlarged pictorial representation of a different arrangement of projections on one sheet of the container of the present invention.

Another embodiment of the projections which may be used in the present invention is shown in FIG. 5. In this embodiment, each of the projections 28 has the same identical shape, such as a generally pyramidal shape which extends from the surface of the sheet 14 gradually inward to an apex. Further, the projections 28 are spaced a constant distance apart to form a grid-like pattern. A plurality of gas flow paths 29 are formed between adjacent, spaced projections 28.

Figure 6:
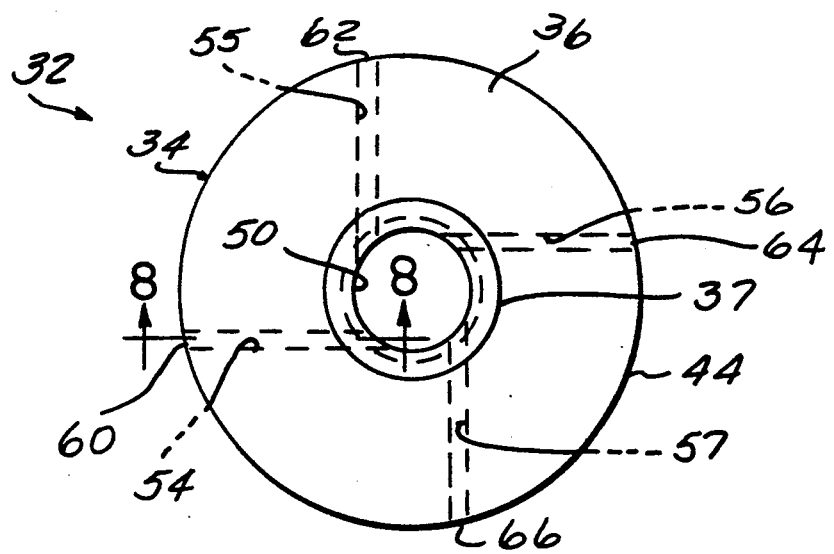
FIG. 6 is a plan view of an internal mixing fitting according to the teachings of the present invention.
Figure 7:
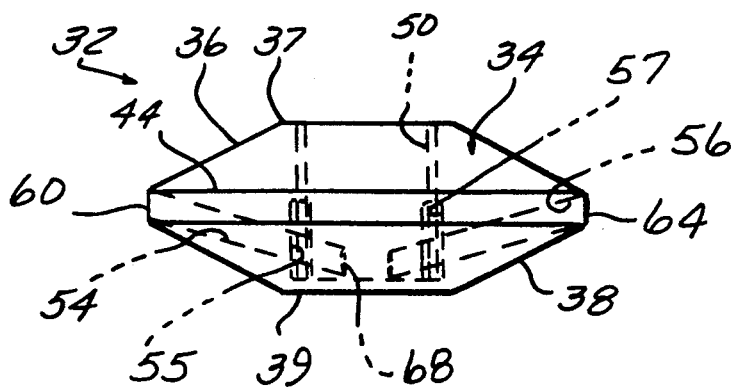
FIG. 7 is a side elevational view of the fitting shown in FIG. 6.
Figure 8:
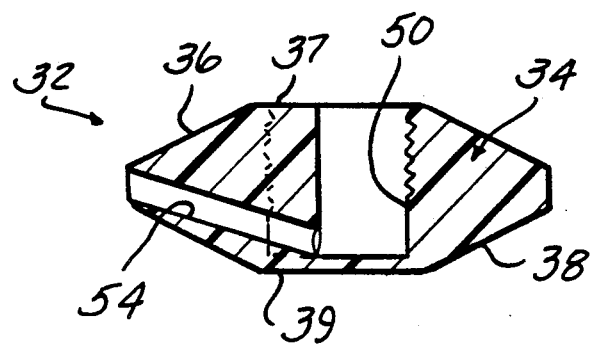
FIG. 8 is a cross sectional view generally taken along line 8—8 in FIG. 6.

An internal mixing fitting 32, as shown in FIGS. 1 and 4 and in greater detail in FIGS. 6, 7 and 8, is mounted within the sealed container 10 for controlling the flow of gas to and from the interior 22 of the sealed container 10. The fitting 32 comprises a body 34 formed of a chemically inert material. Any suitable material, such as a fluorocarbon or fluorinated plastic may be employed. By way of example, fluorocarbons sold under the trademark TEFLON and those sold under trade or chemical names of TFE, PTFE, FEP, PFA and ECTFE, may be employed. Other fluorocarbonated plastics sold under the trademarks FLOUNS, HALARS and KYNAR may be employed. Additionally, polyvinylfluorines, sold under the trademark TEDLAR or trade names, PVF and PV2F, may also be employed.

The body 34 of the fitting 32 has a generally circular shape in plan, as shown in FIG. 1. The body 34 includes a top surface 36 and an opposed, spaced bottom surface 38.

A centrally located planar portion 37 is formed in the top surface 36, with the remainder of the top surface 36 curving or tapering smoothly from the top portion 37 radially outward to a peripheral edge or rim 44. Similarly, a centrally located planar portion 39 is formed in the bottom surface 38. The remaining portion or walls of the bottom surface 38 curve or taper smoothly radially outward from the planar portion 39 to the peripheral edge or rim 44. The peripheral edge or rim 44 is thus spaced between the top and bottom portions 36 and 38, respectively, and extends circumferentially around the body 34.

A first bore 50 is centrally located in the top surface 36 of the body 34 and extends through the planar portion 37 of the top surface 36 into the interior of the body 34. The bore 50 may be internally threaded. For additional strength, an internally threaded metallic sleeve, not shown, can be mounted within the bore 50.

A plurality of second bores, such as second bores 54, 55, 56 and 57, are formed in the body 34. The second bores 54, 55, 56 and 57 extend through the body 34 and are connected in fluid flow communication with the first bore 50 in the body 34, as shown in FIGS. 4, 6, 7 and 8.

Any number of second bores 54, 55, 56 and 57 may be provided in the fitting 32. Further, the second bores may be provided at any angular spacing to provide even gas flow to all portions of the interior cavity 22 of the sealed container 10.

As shown in FIG. 6, each of the second bores 54, 55, 56 and 57 is oriented tangential to the first bore 50 and extends radially outward from the first bore 50 to the peripheral edge or rim 44 of the body 34. This tangential arrangement of the second bores 54, 55, 56 and 57 serves two functions. First, during the flow of gas through the first bore 50 and each of the second bores 54, 55, 56 and 57, either into the sealed container 10 or out of the sealed container 10, the gas swirls through the tangential orientation of the second bores 54, 55, 56 and 57 with respect to the first bore 50. This provides thorough mixing of the gas and averages the gas during evacuation of the gas from the sealed container 10 as the gas is drawn from all portions of the sealed container 10. Secondly, the tangential orientation of the bores 54, 55, 56 and 57 insure that gas stored within the sealed container 10 is drawn evenly from all portions of the sealed container 10 thereby avoiding any stratification of the gas which may have occurred during its storage within the sealed container 10. The swirling action imparted by the tangential arrangement of the second bores 54, 55, 56 and 57 to the first bore 50 as the gas flows from each of the second bores into the first bore 50 insures that the gas from all portions of the container 10 is evenly mixed and averaged before flowing out of the fitting 32.

As shown in FIG. 6–8, a gas flow port is associated with the outer end of each of the second bores. Thus, gas flow ports 60, 62, 64 and 66 are formed at the outer ends of each of the second bores 54, 55, 56 and 57, respectively, at the peripheral edge or rim 44 of the body 34. The gas flow ports 60, 62, 64 and 66 dispose each of the second bores 54, 55, 56 and 57, respectively, in fluid flow communication with the interior cavity 22 in the sealed container 10

As shown more clearly in FIGS. 7 and 8, a first end, such as a first end 68 for the second bore 54, is disposed in fluid flow communication with a bottom portion of the first bore 50 in the body 34. Each of the second bores 54, 55, 56 and 57 extends linearly and radially outward from its first end, such as the first end corresponding to the first end 68 of the second bore 54, to the associate gas flow port at the peripheral edge 44 of the body 34. Although each of the second bores 54, 55, 56 and 57 may extend horizontally from the first bore 50, each of the second bores 54, 55, 56 and 57 is preferably disposed at a predetermined acute angle with respect to the longitudinal axis of the first bore 50 as shown in FIGS. 7 and 8. The angle may be any predetermined angle, with an angle of 75° with respect to the longitudinal axis of the first bore 50 being used as an example only.

In use, the fitting 32 is connected to the source of gas emissions and/or emission test apparatus by means of a coupling denoted generally by reference number 90 in FIGS. 1 and 4. The coupling 90 is preferably, and by way of example only, formed of a nut 92 and a hollow body 94. The body 94 is shown as having a generally elbow shape; although a straight shape for the body 94 may also be provided. The body 94 includes a hollow interior bore 96 which extends between opposed ends of the body 94. The first end 98 of the body 94 is provided with a plurality of external threads which are threadingly engageable with the threads in the first bore 5 in the fitting 32 to attach the body 94 to the fitting 32. A seal means, such as an 0-ring 100, is mounted in a recess at the end of the threaded first end portion 98 of the body 94 for sealingly contacting the upper sheet 12 of the sealed container 10 to sealingly connect the body 94 to the sealed container 10 and to sealingly close the aperture 13 in the top sheet 12 of the container 10. The second end 102 of the body 94 is also provided with a plurality of external threads 104.

Further, as shown in FIGS. 1 and 4, a seal gasket or member 114 is mounted o the exterior surface of the sheet 12 about the aperture in the sheet 12. The gasket 114, which may be formed of a suitable flexible material, also includes a central aperture for receiving the threaded end 98 of the coupling 94 therethrough and serves to seal the coupling 94 to the sheet 12 in conjunction with the O-ring 100 as well as to provide additional strength to the portion of the sheet 12 surrounding the coupling 90.

The nut 92 includes a central, through bore 106 which is adapted to slidingly receive one end of a hollow conduit or tube 108. The conduit 108 is attached at an opposite end to the test equipment for the supply of gas emissions to the apparatus of the present invention and/or to connect such stored gas emissions to test equipment for analysis. The nut 92 may be any conventional nut, such as one disclosed in U.S. Pat. No. 3,977,708 and manufactured by Fluoroware, Inc. The contents of this patent are incorporated herein by reference with respect to the construction of the nut 92.

As shown in FIG. 4, the nut 92 includes a plurality of internal threads 110 which threadingly engage the external threads 104 on the second end 102 of the body 94. Further, the nut 92 includes an internal, elongated, relatively thin sleeve 112. The side walls of the sleeve 112 taper inwardly from one end to a terminal end and are spaced from the opposed threads 110. This arrangement captures the end of the conduit 108 as the nut 92 is threaded onto the second end 102 of the body 94 to sealingly connect the conduit 108 to the body 94.

In use, the sealed container 10 is initially completely evacuated of any gaseous contents such that the top and bottom sheets 12 and 14 are substantially in registry with each other and conform to the smoothly curved top and bottom surfaces 36 and 38 on the fitting 32. The gas conduit 108, shown in FIG. 4, is then connected to a suitable source of gas emissions, such as the engine of a motor vehicle under test. The other end of the conduit 108 is connected to the body 94 after the body 94 has been sealingly threaded to the fitting 32 into sealed engagement with the top sheet 12 adjacent the aperture 13 in the top sheet 12.

Then, gas emissions from the motor vehicle are supplied through the conduit 108, the body 94 and the fitting 32 into the interior cavity 22 of the sealed container 10. The sealed container 10 inflates to a constant volume and, due to the sealed nature of the container 10, sealing retains the gas emissions when the conduit 108 or the coupling 90 is sealingly closed.

Subsequently, when it is desired to analyze the contents of the gas emissions stored within the sealed container 10, such gaseous contents are evacuated from the sealed container 10 through the fitting 32, the body 94 and the conduit 108 to suitable test equipment.

During the inflation and evacuation of the container 10, the gas flow paths 26 or 29 formed between adjacent projections 24 and 28, respectively, insure that the gas flows evenly to and from all portions of the interior cavity 22 of the container 10. In this manner, the container 10 can be repeated inflated to a known, constant volume, with the gas contents completely evacuated at the constant volume for accurate test results.

The fitting 32 may be used with a variety of different couplings, other than the coupling 90 described above and shown in FIGS. 1 and 4. As shown in FIG. 9, a coupling 120 may also be employed with the fitting 32. The coupling 120 includes a body 122 having an internal, through bore 124 formed therein. The body 122 has an elongated shaft portion with a plurality of external threads 126 formed thereon which engage the internal threads in the bore 50 the fitting 32 to attach the body 122 to the fitting 32 with the shaft portion of the body 122 extending outward from the fitting 32 through the apertures in the sheet 12 and the reinforcement member. The body 122 has an enlarged diameter head with an internal recess 128. A suitable seal means, such as an O-ring 130, is mounted in the recess 128 for sealing engagement with the sheet 12 when the body 122 is threadingly engaged with the fitting 32.

The outer lip 131 of the head extends downward below the O-ring 130 for a short distance. This results in the material of the sheet 12 and the reinforcement member 114 surrounding the apertures to be brought into secure engagement with the O-ring 130 when the body 122 is threadingly engaged with the fitting 32.

A straight coupler member 132 is provided with a through bore 133. Threads 134 formed on One end of the coupler member 130 threadingly engage internal threads 136 formed in the enlarged head portion of the body 122 for threading attachment of the coupler member 130 to the body 122. The other end of the coupler member 130 is provided with a reduced diameter and external threads 138 which threadingly engage internal threads 140 formed in a cap member 142. The cap member 142 includes an internal sleeve 144 which securely and sealingly receives a conduit 146 extending to the vehicle under test or to gas emission test apparatus to provide a gas flow path through the coupling 120 and the fitting 32.

Another coupling 150 which may be used with the fitting 32 is shown in FIG. 10. The coupling 150 includes a body 152 substantially identical to the body 122 described above and shown in FIG. 9. The body 152 threadingly engages the threads in the fitting 32 and is sealed thereto by a seal member, such as an O-ring 154. Internal threads 156 formed at one end of the body 152 threadingly receive external threads 158 on a 90° elbow 160. The elbow 160 has an internal bore 162 which forms a flow path with a bore 164 in the body 152 and the bore 50 in the fitting 32 as described above. External threads 166 formed at an opposite end of the elbow 160 threadingly engage a cap 170 which is substantially identical to the cap 142 shown in FIG. 10. The cap 170 sealingly receives one end of a conduit 172 to form a gas flow path between the conduit 172, the coupling 150 and the fitting 32.

In FIG. 11, another coupling 180 is depicted for use with the fitting 32 of the present invention. The coupling 180 includes a body 182 having a threaded end 184 which engages the internal threads in the bore 50 of the fitting 32. An 0-ring 186 is mounted in an enlarged central portion in the body 182 for sealing attachment of the body 182 to the sheet 12 and the reinforcement member 114.

The body 182 includes an elongated, shaft portion 188 which sealingly receives a conduit 190 thereover in a press fit. The conduit 190 is disposed in gas flow communication with the fitting 32 by a central bore 192 formed in the body 182.

The container and fitting of the present invention is uniquely suited for use in gas emission sample apparatus. By forming at least one sheet of the container with a plurality of inward facing projections, with gas flow paths formed between adjacent, spaced projections, the container may be inflated to a known predetermined volume and completely evacuated of the known, predetermined volume gaseous content without the need for gas conduits as utilized in previous devised gas emission sample containers. The internal mixing fitting used in the gas emission sample container of the present invention provides unique mixing of gas flowing through the fitting during storage of the gas within the sealed container and, also during evacuation of the gas for subsequent testing. The tangential arrangement of the second bores in the fitting disperse the gas to all portions of the sealed container and, during evacuation, draw the gas from all portions of the container and impart a swirling action to the gas as it enters the first bore to assure thorough mixing or averaging of the gas and to thereby avoid the adverse effects of any gas stratification which may have occurred during storage. The container and fitting of the present invention is particularly suited for use in small volume containers which previously, due to size or economics, did not employ gas flow conduits within the interior of the container. The container and fitting of the present invention are simply constructed and have a low manufacturing cost.

What is claimed is:

1. A gas emission sample apparatus for receiving and storing gas emissions from a test apparatus, the gas emission storage apparatus comprising:
    a container in the form of a sealed, expansible member having flexible side walls and an aperture formed therein; and
    a fitting disposed in the container, the fitting comprising:
        a generally solid body having a circular plan shape with top and bottom surfaces;
        a first bore formed in the body extending through the top surface into the interior of the body; and
        a plurality of spaced, elongated second bores formed in the body, each of the second bores disposed in fluid flow communication with the first bore at a first end and extending tangentially from the first bore radially outward through the body into fluid flow communication at a second end with the interior of the sealed container.

2. The gas emission sample apparatus of claim 1 wherein the second bores are circumferentially spaced about the body of the fitting.

3. The gas emission sample apparatus of claim 1 wherein four second bores are formed in the body of the fitting.

4. A gas emission sample apparatus for receiving and storing gas emissions from a test apparatus, the gas emission storage apparatus comprising:
    a container in the form of a sealed, expansible member having an aperture formed therein; and
    a fitting disposed in the container, the fitting comprising:
        a body having a circular plan shape with top and bottom surfaces;
        planar top and bottom portions formed in the top and bottom surfaces, respectively, of the body of the fitting, the remaining portions of the top and bottom surfaces smoothly extending from the planar top and bottom portions to a peripheral edge of the body
        a first bore formed in the body extending through the top surface into the interior of the body; and
        a plurality of spaced, second bores formed in the body, the second bores disposed in fluid flow communication with the first bore and extending tangentially from the first bore radially outward through the body into fluid flow communication with the interior of the sealed container.

5. The gas emission sample apparatus of claim 1 wherein:
    the second bores are disposed at an acute angle with respect to a plane extending perpendicular to the longitudinal axis of the first bore in the body of the fitting.

6. A gas emission sample apparatus for receiving and storing gas emissions from a test apparatus, the gas emission storage apparatus comprising:
    a container in the form of a sealed, expansible member having an aperture formed therein; and
    a fitting disposed in the container, the fitting comprising:
        a body having a circular plan shape with top and bottom surfaces;
        planar top and bottom portions formed in the top and bottom surfaces, respectively, of the body of the fitting, the remaining portions of the top and bottom surfaces smoothly extending from the planar top and bottom portions to a peripheral edge of the body;
        a first bore formed in the body extending through the top surface into the interior of the body; and
        a plurality of spaced, second bores formed in the body, the second bores disposed in fluid flow communication with the first bore and extending tangentially from the first bore radially outward through the body into fluid flow communication with the interior of the sealed container, the second bores circumferentially spaced about the body of the fitting, each of the second bores being disposed at a predetermined acute angle with respect to the longitudinal axis of the first bore.

7. A gas emission sample apparatus for receiving and storing gas emissions from a test apparatus, the gas emission storage apparatus comprising:
    a container in the form of a sealed, expansible member having an aperture formed therein, the container including:
        first and second flexible sheets;
        the first and second sheets being sealing joined together at their peripheral edges to form a hollow, internal cavity therebetween; and
        at least one of the first and second sheets having a plurality of discrete, spaced projections formed therein, the projections extending outward from one major surface of the at least one sheet toward the other of the first and second sheets when the first and second sheets are joined together, with gas flow paths formed between adjacent projections over substantially the entire surface of the at least one sheet; and
    a fitting disposed in the container, the fitting including:
        a body having a circular plan shape with top and bottom surfaces;
        a first bore formed in the body extending through the top surface into the interior of the body; and
        a plurality of spaced, second bores formed in the body, the second bores disposed in fluid flow communication with the first bore and extending tangentially from the first bore radially outward through the body into fluid flow communication with the interior of the sealed container.

8. The gas emission sample apparatus of claim 7 wherein the projections are irregularly shaped and irregularly spaced over the at least one sheet.

9. The gas emission sample apparatus of claim 7 wherein the projections are identically shaped and spaced at an identical distance over the at least one sheet.

10. The gas emission sample apparatus of claim 7 wherein both of the first and second sheets have a plurality of discrete, spaced projections formed therein, the projections facing the projections on the other sheet when the first and second sheets are joined together.

11. The gas emission sample apparatus of claim 7 wherein the first and second sheets are formed of an inert plastic.

12. The gas emission sample apparatus of claim 7 further comprising:
- a coupling connected to the fitting and extending through the aperture in the one of the first and second sheets for providing a fluid flow path through the fitting between the interior cavity of the container and one of a source of gas emissions and a gas test apparatus.

13. The gas emission sample apparatus of claim 12 wherein the coupling further comprises:
- a body having a through bore extending therethrough;
- the body including external threads formed at one end, threadingly engageable with the first bore in the body of the fitting;
- seal means mounted on the body and sealingly engageable with one of the flexible sheets when the body is threadingly engaged with the fitting; and
- a coupler member threadingly engageable with the body and sealingly connectible to a conduit.

14. The gas emission sample apparatus of claim 13 wherein:
- the coupler member includes an internal, linear bore extending between opposite ends thereof.

15. The gas emission sample apparatus of claim 13 wherein:
- the coupler member and an internal bore disposed therethrough have a 90° angle between opposed ends thereof.

16. The gas emission sample apparatus of claim 13 wherein the body of the coupling further comprises:
- an enlarged diameter head formed intermediately on the body and spaced from the one end of the body;
- an annular recess formed in the head, the seal means mounted in the recess; and
- an annular peripheral lip formed on the head and extending below the seal means.

17. The gas emission sample apparatus of claim 7 wherein the other of the first and second sheets is smooth.

18. The gas emission sample apparatus of claim 7 wherein:
- the second bores are circumferentially spaced about the body of the fitting;
- each of the second bores being disposed at a predetermined acute angle with respect to the longitudinal axis of the first bore; and
- both of the first and second sheets have a plurality of discrete, spaced projections formed therein, the projections facing the projections on the other sheet when the first and second sheets are joined together;
- an aperture formed in one of the first and second sheets; and
- a coupling sealingly mounted in the aperture in the one of the first and second sheets for providing a fluid flow path between a source of gas emissions and the fitting in the interior cavity of the container.

* * * * *